United States Patent [19]

Dörschug

[11] Patent Number: 5,177,058
[45] Date of Patent: Jan. 5, 1993

[54] PHARMACEUTICAL FORMULATION FOR THE TREATMENT OF DIABETES MELLITUS

[75] Inventor: Michael Dörschug, Bochum, Fed. Rep. of Germany

[73] Assignee: Hoechst Aktiengesellschaft, Frankfurt am Main, Fed. Rep. of Germany

[21] Appl. No.: 392,559

[22] Filed: Aug. 11, 1989

[30] Foreign Application Priority Data

Aug. 13, 1988 [DE] Fed. Rep. of Germany ........ 3827533

[51] Int. Cl.⁵ ............................................. A61K 37/26
[52] U.S. Cl. .......................................... 514/4; 514/3; 530/304; 530/303
[58] Field of Search .................... 514/3, 4; 530/304

[56] References Cited

U.S. PATENT DOCUMENTS

| | | | |
|---|---|---|---|
| 2,143,591 | 1/1939 | Scott et al. | 514/3 |
| 2,354,211 | 7/1944 | Lang et al. | 514/4 |
| 4,608,364 | 8/1986 | Grau | 514/4 |
| 4,652,547 | 3/1987 | Chance et al. | 514/4 |
| 4,701,440 | 10/1987 | Grau | 514/3 |

FOREIGN PATENT DOCUMENTS 0194864 9/1986 European Pat. Off. .
0132770 9/1987 European Pat. Off. .
0132769 1/1988 European Pat. Off. .
0254516 1/1988 European Pat. Off. .

OTHER PUBLICATIONS

Scott et al., "The Effect of Zinc Salt on the Action of Insulin," J. Pharmakol. 55 (1935) pp. 206–221.

Primary Examiner—Robert A. Wax
Assistant Examiner—Richard C. Ekstrom
Attorney, Agent, or Firm—Finnegan, Henderson, Farabow, Garrett and Dunner

[57] ABSTRACT

Pharmaceutical formulations for the treatment of diabetes mellitus are disclosed, wherein the pharmaceutical formulations contain at least one insulin derivative modified with a base in position B31 of the insulin B chain and having an isoelectric point between 5.8 and 8.5 and/or at least one of its physiologically tolerated salts in a pharmaceutically acceptable excipient and a relatively high zinc ion content in the range from above 1 μg to about 200 μg of zinc/IU. The preferred insulin derivative modified with a base for this pharmaceutical formulation is human insulin-B31-Arg-OH and human insulin-B31-Arg-B32-Arg-OH. The formulation is used for the treatment of diabetes mellitus; it has a particularly favorable action profile.

11 Claims, No Drawings

PHARMACEUTICAL FORMULATION FOR THE TREATMENT OF DIABETES MELLITUS

DESCRIPTION

Diabetes mellitus today is predominantly treated by parenteral administration of formulations of the hormone insulin, which lowers the blood sugar. The aim of this therapy is to bring the human organism as close as possible to the state of its natural hormone equilibrium, that is to say to "stabilize" the patient as optimally as possible, since in the event of non-optimum "stabilization", in addition to immediate consequences such as hyper- or hypoglycemia, diabetic delayed complications can be expected in particular, which include, inter alia, retinopathy, neuropathy, nephropathy and micro- and macroangiopathy.

Because of the diversity of the human individuals-and hence of course also of the diabetes mellitus patients-it is necessary to have available a large number of insulin formulations with various action characteristics for the optimum possible "stabilization" of the patients.

Because of the specific nature of insulin and its metabolism, the duration of the action of a simple insulin solution is only very short, so that for permanent control of the blood sugar of diabetics either several daily injections or a continuous infusion using metering units are needed, or an insulin formulation having a delayed action must be administered.

In the case of non-modified insulin in dissolved form (at an acid pH), a delay profile can be achieved by the presence of large amounts of zinc ions—for example 0.4–1 mg/IU (=international unit) of insulin; compare J Pharmakol. 55 (1935), page 206. However, such large amounts of zinc cause pain during administration, so that such insulin solutions with such high zinc contents have not been used in diabetes therapy.

Those states of insulin which are sparingly soluble at the injection site are of considerable therapeutic importance as delay principles. These include, for example, zinc-insulin crystals or protamine-insulin crystals, which release insulin over a certain period of time while slowly dissolving again. The customary delay suspensions of zinc-insulin crystals or zinc-protamine-insulin must be mixed homogeneously before administration.

Another advantageous delay principle is represented by the insulin derivatives modified with bases in accordance with EP-B-0,132,770. These are derivatives modified with bases specifically in position B31 of the insulin B chain and having an isoelectric point between 5.8 and 8.5. The corresponding pharmaceuticals contain at least one insulin derivative-modified by a base in position B31-of the following formula I and/or at least one of its physiologically tolerated salts as the active compound; formula I is

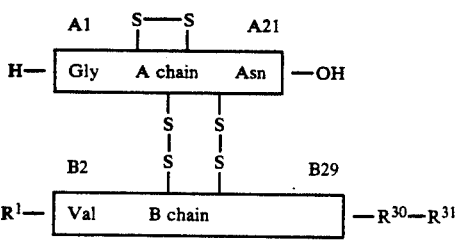

in which $R^1$ denotes H or H-Phe, $R^{30}$ represents the radical of a neutral, genetically encodable L-amino acid and $R^{31}$ represents a physiologically acceptable organic group of basic character having up to 50 carbon atoms, in the build-up of which 0 to 3 α-amino acids participate and in which any terminal carboxyl function present can be free, in the ester function form, in the amide function form, in the lactone form or reduced to $CH_2OH$.

The delay or depot action of these insulin derivatives modified by bases is attributed to an intrinsic physical principle related to protein chemistry, i.e. the sparingly soluble nature of the insulin derivative at its isoelectric point. According to the abovementioned EP-B-0,132,770, redissolving under physiological conditions is said to be achieved by detachment of the additional basic groups, which arises, depending on the derivative, by tryptic or trypsin-like and/or carboxypeptidase B or carboxypeptidase B-like and/or esterase activity. The particular groups detached are either purely physiological metabolites or readily metabolizable, physiologically acceptable substances.

The pharmaceutical formulations of these insulin derivatives modified with bases can be free from zinc or can also contain up to 100 μg of zinc/100 IU (=1 μg of zinc/IU).

According to EP-B-0,132,769, the insulin derivatives modified with bases in the B31 position of the insulin B chain, and physiologically tolerated salts thereof, can also be mixed, inter alia, with non-modified insulin and-/or physiologically acceptable salts thereof; the corresponding pharmaceutical formulations have an action profile which is composed of the action profiles of the individual active compounds.

These mixed formulations can also be free from zinc or have a zinc content of up to 1 μg/IU.

The abovementioned depot principle resulting from modification of insulin with bases has been utilized still further by providing and correspondingly using other insulin derivatives modified with bases—mainly within the A and B chains; cf. EP-A-0,194,864 and EP-A-0,254,516. The pharmaceutical formulations with these specific insulin derivatives modified with bases preferably contain zinc ions in an amount of between 2 μg and about 2 mg/ml, in particular between 5 μg and 200 μg/ml. By mixing a zinc-free active compound solution or suspension with a separate zinc salt solution immediately before administration, the patient can himself, if appropriate, establish a particular different zinc content in the administration form—and thus establish an action profile which is better suited to the circumstances.

In spite of the considerable number of known insulin forms with a rapid and also with a delayed action and also with "mixed" action profiles, because of the individual diversity of the organisms there is a need for further insulin administration forms with other specific action profiles.

In the efforts to provide other such insulin administration forms with specific action profiles, it has now been found that this aim is achieved by increasing the zinc content of the pharmaceutical formulations described in the two abovementioned EP Patents 0,132,770 and 0,132,769.

The invention thus relates to a pharmaceutical formulation containing at least one insulin derivative modified with bases and having an isoelectric point between 5.8 and 8.5, of the formula I already mentioned above, and/or at least one of its physiologically tolerated salts in a pharmaceutically acceptable excipient with a content of zinc ions; in the formulation, the zinc ion content lies in the range from about 1 μg to about 200 μg of zinc/IU, preferably from about 1 to 50 μg of zinc/IU.

It is surprising that the relatively high zinc content here does not lead to complications in the patients. The action profile can be controlled within a wide range by the zinc content within the limits stated and the isotonic agent obligatory in such formulations. The combination of high zinc contents and certain isotonic agents which keep the insulin derivative in solution in the weakly acid medium in spite of the high zinc content is particularly advantageous here. A weakly acid pH range is advantageous because of the known long-term stability in this range of the insulin derivatives, with which the formation of derivatives is known to occur (in particular deamidation of $Asn^{A21}$) under more acid conditions. The insulin derivatives employed here furthermore have their full biological activity in the presence of high zinc concentrations.

The insulin derivatives, modified with bases, of the formula I which are suitable for the formulation according to the invention are the insulin derivatives modified with bases in position B31 such as are described in the abovementioned publications EP-B-0,132,770 and EP-B-0,132,769 for the pharmaceuticals therein with or without a lower zinc content. They are thus compounds of the formula I in which $R^1$ denotes H or H-Phe, $R^{30}$ represents the radical of a neutral, genetically encodable L-amino acid and $R^{31}$ represents a physiologically acceptable organic group of basic character having up to 50 carbon atoms, in the build-up of which 0 to 3 α-amino acids participate and in which any terminal carboxyl function present can be free, in the ester function form, in the amide function form, in the lactone form or reduced to $CH_2OH$.

$R^1$ is preferably H-Phe.

Neutral, genetically encodable L-amino acids—for $R^{30}$—are Gly, Ala, Ser, Thr, Val, Leu, Ile, Asn, Gln, Cys, Met, Tyr, Phe and Pro; Ala, Ser and Thr, especially Thr, are preferred.

$R^{31}$ is a physiologically acceptable organic group of basic character having up to 50 carbon atoms, in the build-up of which 0–3 α-amino acids participate. If no α-amino acids participate in the build-up of $R^{31}$, the following basic groups, for example, are possible for this radical: amino-($C_2$ to $C_6$)-alkoxy, ($C_1$ to $C_4$)-alkylamino-($C_2$ to $C_6$)-alkoxy, di-($C_1$ to $C_4$)-alkylamino-($C_2$ to $C_6$)-alkoxy, tri-($C_1$ to $C_4$)-ammonio-($C_2$ to $C_6$)-alkoxy, amino-($C_2$ to $C_6$)-alkylamino, [($C_1$ to $C_4$)-alkylamino]-($C_2$ to $C_6$)-alkylamino, [di-($C_1$–$C_4$)-alkylamino]-($C_2$–$C_6$)-alkylamino or [tri-($C_1$ to $C_4$)-alkylamino]-($C_2$ to $C_6$)-alkylamino, in particular $-O-[CH_2]_p-NR_2$, $-O-[CH_2]_p-N^+R_3$, $-NH-[CH_2]_p-NR_2$ or $-NH-[CH_2]_p-N^+R_3$, in which p is 2 to 6 and the radicals R are identical or different and represent hydrogen or ($C_1$ to $C_4$)-alkyl.

If up to 3 α-amino acids participate in the build-up of $R^{31}$, these are primarily neutral or basic naturally occurring L-amino acids and/or the D-amino acids corresponding to these. Neutral naturally occurring amino acids are, in particular, Gly, Ala, Ser, Thr, Val, Leu, Ile, Asn, Gln, Cys, Met, Tyr, Phe, Pro and Hyp. Basic naturally occurring amino acids are, in particular, Arg, Lys, Hyl, Orn, Cit and His. If only neutral α-amino acids participate, their terminal carboxyl function—so that $R^{31}$ has a basic character—cannot be free; rather, the carboxyl function must in this case be esterified or amidated with a basic group, possible such basic groups being, for example, the basic groups mentioned above—in the case where no α-amino acids participate in the build-up of $R^{31}$. These basic ester or amide groups can of course also block the carboxyl function of basic α-amino acids. Neutral ester or amide groups, such as, for example, ($C_1$ to $C_6$)-alkoxy, ($C_3$ to $C_6$)-cycloalkoxy, $NH_2$, ($C_1$ to $C_6$)-alkylamino or di-($C_1$ to $C_6$)-alkylamino can be suitable for blocking the carboxyl function of the basic α-amino acids-if blocking is desirable.

The terminal carboxyl function can of course be present in the lactone form only if the terminal amino acid is a hydroxyamino acid.

The terminal carboxyl function can also be reduced to $CH_2OH$.

$R^{31}$ is preferably composed of 1, 2 or 3 of the abovementioned basic naturally occurring amino acids; $R^{31}$ is particularly preferably Arg-OH or Arg-Arg-OH.

The (A1 to A21) and the (B2 to B29) sequences of the insulin derivatives of the formula I are preferably the sequences of human, porcine or bovine insulin, in particular the sequences of human insulin.

Concrete insulin derivatives, modified with bases, of the formula I are, for example:
human insulin-$Arg^{B31}$-OH
human insulin-$Arg^{B31}$-$Arg^{B32}$-OH
de-$Phe^{B1}$-porcine insulin-$Arg^{B31}$-OH
de-$Phe^{B1}$-human insulin-$Arg^{B31}$-OH
de-$Phe^{B1}$-porcine insulin-$Arg^{B31}$-$Arg^{B32}$-OH
de-$Phe^{B1}$-human insulin-$Arg^{B31}$-$Arg^{B32}$-OH
porcine insulin-$Arg^{B31}$-$OCH_3$
human insulin-$Arg^{B31}$-$OCH_3$
bovine insulin-$Arg^{B31}$-$OCH_3$
porcine insulin-$Arg^{B31}$-$Arg^{B32}$-$OCH_3$
human insulin-$Arg^{B31}$-$Arg^{B32}$-$OCH_3$
de-$Thr^{B30}$-human insulin-$Val^{B30}$-$Arg^{B31}$-OH
de-$Thr^{B30}$-human insulin-$Val^{B30}$-$Ala^{B31}$-$Arg^{B32}$-OH
human insulin-$Lys^{B31}$-OH
human insulin-D-$Arg^{B31}$-OH
human insulin-D-$Arg^{B31}$-$Arg^{B32}$-OH
human insulin-$Arg^{B31}$-D-$Arg^{B32}$-OH
human insulin-$Lys^{B31}$-$Arg^{B32}$-OH
human insulin-$Arg^{B31}$-$Lys^{B32}$-OH
human insulin-argininol$^{B31}$
human insulin-$Val^{B31}$-$Arg^{B32}$-OH
human insulin-$Val^{B31}$-$Arg^{B32}$-$Arg^{B33}$-OH
human insulin-$Arg^{B31}$-argininol$^{B32}$
human insulin-$Lys^{B31}$-$Arg^{B32}$-$Arg^{B33}$-OH

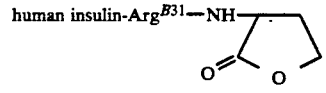

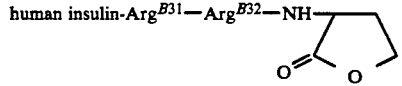

human insulin-$Arg^{B31}$-$NH_2$
human insulin-$Arg^{B31}$-$Arg^{B32}$-$NH_2$
human insulin-$Orn^{B31}$-OH
human insulin-$Leu^{B31}$-$Cit^{B32}$-OH
human insulin-(B30)-$OCH_2CH_2$-$NH_2$ human insulin-(B30)-NH-CH$_2$CH$_2$-NH$_2$
human insulin-Arg$^{B31}$-O-CH$_2$-CH$_2$-NH$_2$
human insulin-Arg$^{B31}$-CH$_2$-CH$_2$-N(CH$_3$)$_2$
human insulin-(B30)-O-CH$_2$-CH$_2$-N(CH$_3$)$_3$
human insulin-(B30)-NH-CH$_2$-CH$_2$-N(CH$_3$)$_3$
human insulin-Leu$^{B31}$-O-CH$_2$-CH$_2$-CH$_2$-N(C$_2$H$_5$)$_3$
human insulin-Trp$^{B31}$-Trp$^{B32}$-Trp$^{B33}$-NH(CH$_2$)$_6$-N((CH$_2$)$_3$CH$_3$)$_3$ The physiologically tolerated salts of these insulin derivatives modified with bases can also be used.

The zinc ion content is effected by zinc salts, such as, for example, ZnCl$_2$, ZnSO$_4$ and the like.

The pharmaceutical formulation according to the invention can otherwise be built up in the same way as is also described for the pharmaceuticals in the above-mentioned EP-B-0,132,770 and EP-B-0,132,769. It has a pH of preferably between about 2.5 and 8.5, in particular between about 4.0 and 8.5, and contains a suitable isotonic agent, a suitable preservative and if appropriate a suitable buffer, all of course in sterile aqueous solution. The entirety of the formulation constituents excluding the active compounds forms the formulation excipient.

Suitable isotonic agents are, for example, glycerol, glucose, NaCl or calcium or magnesium compounds, such as CaCl$_2$, MgCl$_2$ and the like.

The solubility of the insulin derivatives, modified with bases, at the weakly acid pH values is influenced by the choice of the isotonic agent. The presence of a dissolved insulin derivative at only a weakly acid pH is desirable, since less severe formation of derivatives, in particular formation of deamidation products (for example Asn$^{21}$), occurs in this range.

Suitable preservatives are, for example, phenol, m-cresol, benzyl alcohol and/or p-hydroxybenzoic acid esters.

Sodium acetate, sodium citrate or sodium phosphate, for example, can be used as buffer substances, in particular for establishing a pH of between about 4.0 and 8.5. Physiologically acceptable dilute acids (typically HCl) or alkalis (typically NaOH) are otherwise also suitable for establishing the pH.

Non-modified insulin, preferably bovine, porcine or human insulin, in particular human insulin, can also be admixed for the purpose of varying the action profile of the formulation according to the invention.

The following examples are intended to illustrate the invention in more detail:

1. Action profile of an insulin-Arg$^{B31}$—OH formulation on dogs as a function of the Zn$^{2+}$ content
   Composition/ml  40 IU of human insulin-Arg$^{B31}$—OH
                   18.82 mg of glycerol
                   10 mg of benzyl alcohol
                   pH 4.0

Blood sugar in percent of the initial value

|  | Preparation after | 1 H (= hour) | 2 H | 3 H | 5 H |
|---|---|---|---|---|---|
|  | 0 μg of Zn$^{2+}$ (= 0 μg/IU) | 60 |  | 50 | 72 | 110 |
|  | 10 μg of Zn$^{2+}$ (= 0.25 μg/IU) | 51 | 51 | 72 | 98 |
| Comparison | Basal-H-Insulin Hoechst$^{(R)}$, i.e. an NPH (= neutral protamine of Hagedorn) with about 10 μg of Zn$^{2+}$ (= 0.25 μg/IU) | 70 | 62 | 71 | 90 |
| according to the invention | 80 μg of Zn$^{2+}$ (= 2 μg/IU) | 60 | 51 | 52 | 70 |

2. Action profile of an insulin-Arg$^{B31}$—OH formulation on dogs and rabbits as a function of the Zn$^{2+}$ content
   Composition/ml  40 IU of human insulin-Arg$^{B31}$—OH
                   18.82 mg of glycerol
                   10 mg of benzyl alcohol
                   pH 4.0

Blood sugar in percent of the initial value

|  | Preparation | 1 H | 2 H | 3 H | 5 H | 7 H |
|---|---|---|---|---|---|---|
| a) Dog | | | | | | |
|  | 40 μg of Zn$^{2+}$ (= 1.0 μg/IU) | 82 | 60 | 62 | 88 | 93 |
| Comparison | Depot-H-Insulin Hoechst$^{(R)}$ = 75% NPH + 25% human insulin with about 10 μg of Zn$^{2+}$ (= 0.25 μg/IU) | 63 | 51 | 61 | 100 | 101 |
| according to the invention | 80 μg of Zn$^{2+}$ (= 2.0 μg/IU) | 69 | 52 | 51 | 70 | 93 |
|  | 160 μg of Zn$^{2+}$ (= 4.0 μg/IU) | 95 | 68 | 60 | 70 | 82 |
| b) Rabbit | | | | | | |
| Comparison | 40 μg of Zn$^{2+}$ | 51 | 72 | 100 | 99 | 99 |
|  | Depot-H-Insulin Hoechst$^{(R)}$ | 51 | 52 | 71 | 96 | 100 |
| according to the invention | 80 μg of Zn$^{2+}$ (= 2.0 μg/IU) | 50 | 63 | 94 | 110 | 100 |
|  | 160 μg of Zn$^{2+}$ (= 4.0 μg/IU) | 57 | 65 | 94 | 102 | 100 |

3. Action profile of an insulin-Arg$^{B31}$—OH formulation on dogs as a function of the isotonic agent
   Composition/ml  40 IU of human insulin-Arg$^{B31}$—OH
                   10 mg of benzyl alcohol
                   80 μg of Zn$^{2+}$ (= 2.0 μg/IU)
                   pH 4.5

Blood sugar in percent of the initial value

|  | Preparation with isotonic agent: | 1 H | 2 H | 3 H | 5 H | 7 H |
|---|---|---|---|---|---|---|
|  | NaCl | 70 | 61 | 61 | 103 | 105 |
|  | CaCl$_2$ | 71 | 62 | 65 | 99 | 100 |
|  | Glycerol | 70 | 63 | 55 | 80 | 98 |
|  | Glucose | 70 | 61 | 58 | 91 | 108 |
|  | Sodium citrate | 61 | 63 | 80 | 119 | 118 |
| Comparison: | Basal-H-Insulin HOECHST$^{(R)}$ | 71 | 55 | 63 | 85 | 95 |

4. Action profile of an insulin-Arg$^{B31-B32}$—OH formulation on rabbits and on dogs as a function of the Zn$^{2+}$ content
   Composition/ml  40 IU of human insulin-Arg$^{B31-B32}$—OH
                   10 mg of benzyl alcohol
                   18.82 mg of glycerol
                   pH 4.0

Blood sugar in percent of the initial value

|  |  | 1 H | 2 H | 3 H | 5 H | 7 H |
|---|---|---|---|---|---|---|
| a) Dog | | | | | | |
|  | without Zn$^{2+}$ | 59 | 60 | 79 | 105 | 110 |
|  | 5 μg of Zn$^{2+}$ (= 0.125 μg/IU) | 68 | 59 | 77 | 100 | 107 |
| Comparison | Basal-H-Insulin Hoechst$^{(R)}$ | 71 | 49 | 59 | 83 | 100 |
| according to the invention | 80 μg of Zn$^{2+}$ (= 2.0 μg/IU) | 77 | 52 | 64 | 85 | 98 |
| b) Rabbit | | | | | | |
|  | without Zn$^{2+}$ | 43 | 58 | 72 | 92 | 94 |
|  | 5 μg of Zn$^{2+}$ | 75 | 64 | 80 | 99 | 105 |
| Comparison | Basal-H-Insulin Hoechst$^{(R)}$ | 56 | 56 | 71 | 96 | 99 |
| according to the invention | 80 μg of Zn$^{2+}$ (= 2.0 μg/IU) | 63 | 64 | 88 | 95 | 105 |

At the end of the experiments above (7 Hours), the blood sugar values scarcely have any more reliable significance because of the overlapping of several different influences.

I claim:

1. A pharmaceutical formulation containing at least one insulin derivative modified with a base and having an isoelectric point between 5.8 and 8.5, of the formula I

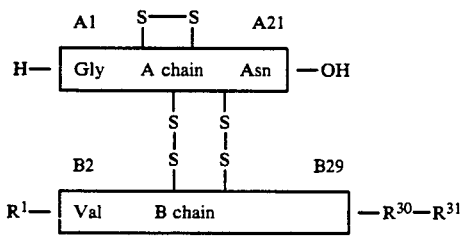

in which $R^1$ denotes H or H-Phe, $R^{30}$ represents the radical of a neutral, genetically encodable L-amino acid and $R^{31}$ represents a physiologically acceptable organic group of basic character having up to 50 carbon atoms, in the build-up of which 0 to 3 α-amino acids participate and in which any terminal carboxyl function present can be free, or reduced to $CH_2OH$, and containing at least one of its physiologically tolerated salts in a pharmaceutically acceptable excipient with a content of zinc ions, in which the zinc ion content is in a range from 4.0 μg to about 200 μg of zinc/IU.

2. A pharmaceutical formulation as claimed in claim 1, wherein $R^1$ in formula I denotes H-Phe.

3. A pharmaceutical formulation as claimed in claim 1, wherein $R^{30}$ in formula I denotes Ala, Ser or Thr.

4. A pharmaceutical formulation as claimed in claim 3, wherein $R^{30}$ in formula I denotes Thr.

5. A harmaceutical formulation as claimed in claim 1, wherein $R^{31}$ in formula I is composed of one, two or three basic naturally occurring amino acids of the series comprising Arg, Lys, Hyl, Orn, Cit and/or His.

6. A pharmaceutical formulation as claimed in claim 5, wherein $R^{31}$ in formula I is Arg-OH or Arg-Arg-OH.

7. A pharmaceutical formulation as claimed in claim 1, wherein the (A1 to A21) and the (B2 to B29) sequences in the insulin derivatives of formula I are the sequences of human, porcine or bovine insulin.

8. A pharmaceutical formulation as claimed in claim 7, wherein the (A1 to A21) and the (B2 to B29) sequences in the insulin derivatives of formula I are the sequences of human insulin.

9. A pharmaceutical formulation as claimed in claim 1, which additionally also contains at least 1 non-modified insulin.

10. A pharmaceutical formulation as claimed in claim 9, wherein the non-modified insulin is human insulin.

11. A method for treating a patient suffering from diabetes mellitus, which comprises administering to said patient a pharmaceutical composition as claimed in claim 1, 9, or 10.

* * * * *

UNITED STATES PATENT AND TRADEMARK OFFICE
CERTIFICATE OF CORRECTION

PATENT NO. : 5,177,058
DATED : January 05, 1993
INVENTOR(S) : Michael Dorschug

It is certified that error appears in the above-identified patent and that said Letters Patent is hereby corrected as shown below:

Claim 5, Column 8, Line 9 change "harmaceutical" to --pharmaceutical--.

Signed and Sealed this

Twenty-first Day of December, 1993

Attest:

BRUCE LEHMAN

Attesting Officer     Commissioner of Patents and Trademarks